United States Patent [19]
Kaufman et al.

[11] Patent Number: 5,547,459
[45] Date of Patent: Aug. 20, 1996

[54] ULTRASONIC BONE-THERAPY APPARATUS AND METHOD

[75] Inventors: Jonathan J. Kaufman, Brooklyn, N.Y.; Alessandro E. Chiabrera, Genoa, Italy

[73] Assignee: Orthologic Corporation, Phoenix, Ariz.

[21] Appl. No.: 329,015

[22] Filed: Oct. 25, 1994

[51] Int. Cl.⁶ .............................. A61N 1/00; A61B 8/00
[52] U.S. Cl. ............................................ 601/2; 128/660.03
[58] Field of Search ..................... 128/660.01, 660.03, 128/661.03; 607/51–52; 601/2

[56] References Cited

U.S. PATENT DOCUMENTS

| | | | |
|---|---|---|---|
| 4,105,017 | 8/1978 | Ryaby et al. | 128/1.5 |
| 4,315,503 | 2/1982 | Ryaby et al. | 128/1.5 |
| 4,530,360 | 7/1985 | Duarte | 607/51 |
| 4,818,697 | 4/1989 | Liboff et al. | 435/173 |
| 4,932,951 | 6/1990 | Liboff et al. | 606/13 |
| 4,993,413 | 2/1991 | McLeod et al. | 128/419 |
| 5,067,940 | 11/1991 | Liboff et al. | 600/13 |
| 5,077,934 | 1/1992 | Liboff et al. | 47/1.3 |
| 5,087,336 | 2/1992 | Liboff et al. | 204/155 |
| 5,088,976 | 2/1992 | Liboff et al. | 600/13 |
| 5,100,373 | 3/1992 | Liboff et al. | 600/13 |
| 5,106,361 | 4/1992 | Liboff et al. | 600/13 |
| 5,143,588 | 9/1992 | Liboff et al. | 204/155 |
| 5,259,384 | 11/1993 | Kaufman et al. | 128/600.01 |
| 5,309,898 | 5/1994 | Kaufman et al. | 601/2 |
| 5,318,561 | 6/1994 | McLeod et al. | 600/14 |

*Primary Examiner*—Francis Jaworski
*Attorney, Agent, or Firm*—Dykema Gossett PLLC

[57] ABSTRACT

A method of ultrasonic bone-therapy subjects a bone to an ultrasonic excitation pulse signal of finite duration, supplied to a transducer next to the bone, and involving a sinusoidal signal in the ultrasonic region to approximately 2 MHz peculiarly modulated by a sinusoidal signal with frequency between about 0 Hz and about 25 kHz; the excitation signal is repeated in the range of 1 to 5000 Hz. The exposure time for therapy is chosen to be in the range of 5 minutes to 1 hour, for 1 to 3 times a day, for a period of days as necessary for healing or for promoting bone growth and ingrowth. An apparatus for implementing the above method for ultrasonic bone therapy is disclosed comprising a transducer having a transmitting and a receiving element, a special waveform signal generator, and a computer for performing the necessary operations defining a preferred treatment regime.

43 Claims, 3 Drawing Sheets

ULTRASONIC BONE-THERAPY APPARATUS AND METHOD

FIELD OF THE INVENTION

The invention pertains to apparatus and method for non-invasively therapeutically treating bone tissue in vivo.

BACKGROUND OF THE INVENTION

In recent years, various attempts have been made to stimulate bone growth. These approaches have been essentially ad hoc, with no consistent framework within which to identify the most effective stimulation.

Kaufman et al., U.S. Pat No. 5,309,808 discloses an apparatus and method for therapeutically treating and/or quantitatively evaluating bone tissue In vivo. The Kaufman method includes subjecting bone to an ultrasonic acoustic signal pulse of finite duration, and involving a composite sine-wave signal consisting of plural discrete frequencies. These frequencies are spaced in the ultrasonic region to approximately 2 MHz; the excitation signal is repeated substantially in the range from 1 to 1000 Hz.

Duarte, U.S. Pat. No. 4,530,360 discloses an apparatus and a method of using ultrasonic energy for therapeutic treatment of bone tissue in vivo, using a pulsed sine wave at substantially a single frequency within the range from 1.3 to 2.0 MHz, and at a pulse repetition rate of 100 to 1000 Hz.

McLeod et al., U.S. Pat. Nos. 5,103,806 and 5,191,880 disclose methods for promoting bone tissue growth and the prevention of osteopenia, using mechanical loading of the bone tissue. In both patents, the inventors apply a mechanical load to the bone tissue at a relatively low level on the order of between about 10 and about 1000 microstrain, peak to peak, and at a frequency in the range of about 10 to 100 Hertz.

Bassett et al., U.S. Pat. No. 4,928,959 disclose a method and device for providing active exercise treatment for a patient suffering from a bone disorder. A patient is subjected to an impact load in order to stimulate bone growth, with an impact load sensor being used to monitor the treatment strength. The inventors noted that high frequency (up to 100,000 Hz) force components were important for stimulating bone growth.

Numerous other patents disclose methods for stimulating bone growth relying on the generation of electromagnetic signals. For example, Ryaby et al., U.S. Pat. Nos. 4,105,017 and 4,315,503 describe methods for promoting bone healing in delayed and nonunion bone fractures, using an asymmetric pulsed waveform. In U.S. Pat. No. 4,993,413, McLeod et al. disclose a method and apparatus for inducing a current and voltage in living tissue to prevent osteoporosis and to enhance new bone formation. They disclose the use of a symmetrical low frequency and low intensity electromagnetic signal substantially in the range of 1–1000 Hertz. In Liboff et al., U.S. Pat. No. 5,318,551 (and others), methods are disclosed that incorporate the combined use of a static and time-varying magnetic field to stimulate bone healing and growth. Specific amplitudes and frequencies are disclosed for optimal enhancement of bone growth, based on the theory of "ion-cyclotron resonance".

A recent publication by Weinbaum et al. provides a comprehensive and theoretically consistent basis to characterize the means by which bone growth occurs. The seminal article "A model for excitation of osteocytes by mechanical loading-induced bone fluid shear stresses," may be found in the *Journal of Biomechanics*, Vol. 27, 1994, pp 339–360. In this publication, they propose that it is not strain magnitude but strain rate that is the primary relevant variable responsible for adaptive bone growth and remodeling.

The prior art, exemplified by the references that have been briefly discussed, have used primarily ad hoc approaches or empirical findings for determining exogenous stimulations used up to now for the promotion of bone growth and healing. Some have focussed on the generation of specific values of biomechanical strain in the tissue as the primary modality of action. However, this invention incorporates the realization that fluid flow induced in normal physiological loading is the critically important variable in bone healing, and moreover, includes an efficient means for generating this fluid flow in living tissues. Specifically, this invention includes a means for stimulating fluid flow at relatively high frequencies by taking unique advantage of the nonlinear characteristics of ultrasound propagation in an ionic-fluid-saturated porous medium such as bone. In addition, this invention incorporates the important features of repetitive stimulation in analogy to that found in normal physiologic loading, and of adaptive feedback control for ensuring that an optimal signal dose arrives at the desired bone tissue site.

SUMMARY OF THE INVENTION

It is an object of this invention to provide an improved method and apparatus for non-invasively therapeutically treating bone tissue in vivo, to promote bone healing and bone growth.

Another object is to meet the above object, such that bone healing and bone growth may be more efficiently and more effectively stimulated than heretofore.

A specific object is to achieve the above objects with an optimal set of ultrasonic signals chosen with respect to the specific nonlinear characteristics of their propagation within the bone tissue and with respect to the emulation of physiological loading.

A further specific object is to enable adaptive and on-line evaluation of the optimal dose of an applied exogenous ultrasonic acoustic therapeutic signal.

It is a general object of the invention to achieve the foregoing objects with apparatus components that are for the most part commercially available.

The invention in its presently preferred form achieves the foregoing objectives by subjecting bone to an ultrasonic acoustic excitation signal pulse of finite duration in the ultrasonic region of approximately 1.1 MHz, supplied to a transducer adapted for acoustic coupling to the skin surface overlying a bone; the excitation signal is repeated in the range of about 1 Hz to about 5000 Hz. The exposure time for therapy is chosen to be in the range of 5 minutes to 1 hour, for 1 to 3 times a day, for a period of days as necessary for complete healing or for promoting bone growth or ingrowth.

Before ultrasonic therapy is started, an initial interrogating acoustic ultrasonic pulse is preferably transmitted in order to determine the actual thickness of soft tissue overlying the bone treatment site. (Note that the thickness may change over time due to tissue swelling, for example.) The bone treatment site may be the zone of fracture, the interface between an implanted device (e.g., hip) and bone, or an intact bone which has reduced bone mass, as for example with osteoporosis. Using the round-trip pulse transmit time between the transducer and the near-bone surface and the nominal attenuation value associated with the soft tissue, the input signal amplitude supplied to the transducer is adjusted to ensure that the spatial-average time-average (SATA) power density (i.e., intensity $I_{SATA}$) reaching the near-bone surface is approximately 45 mW/cm². The received signal is also monitored during the actual treatment exposure to ensure that the patient is receiving the prescribed therapy during the prescribed treatment time.

With these and other objects and advantages in view, the present invention will be clearly understood from the ensuing detailed description in connection with the drawings.

DETAILED DESCRIPTION OF THE PREFERRED EMBODIMENTS

Figure 1:
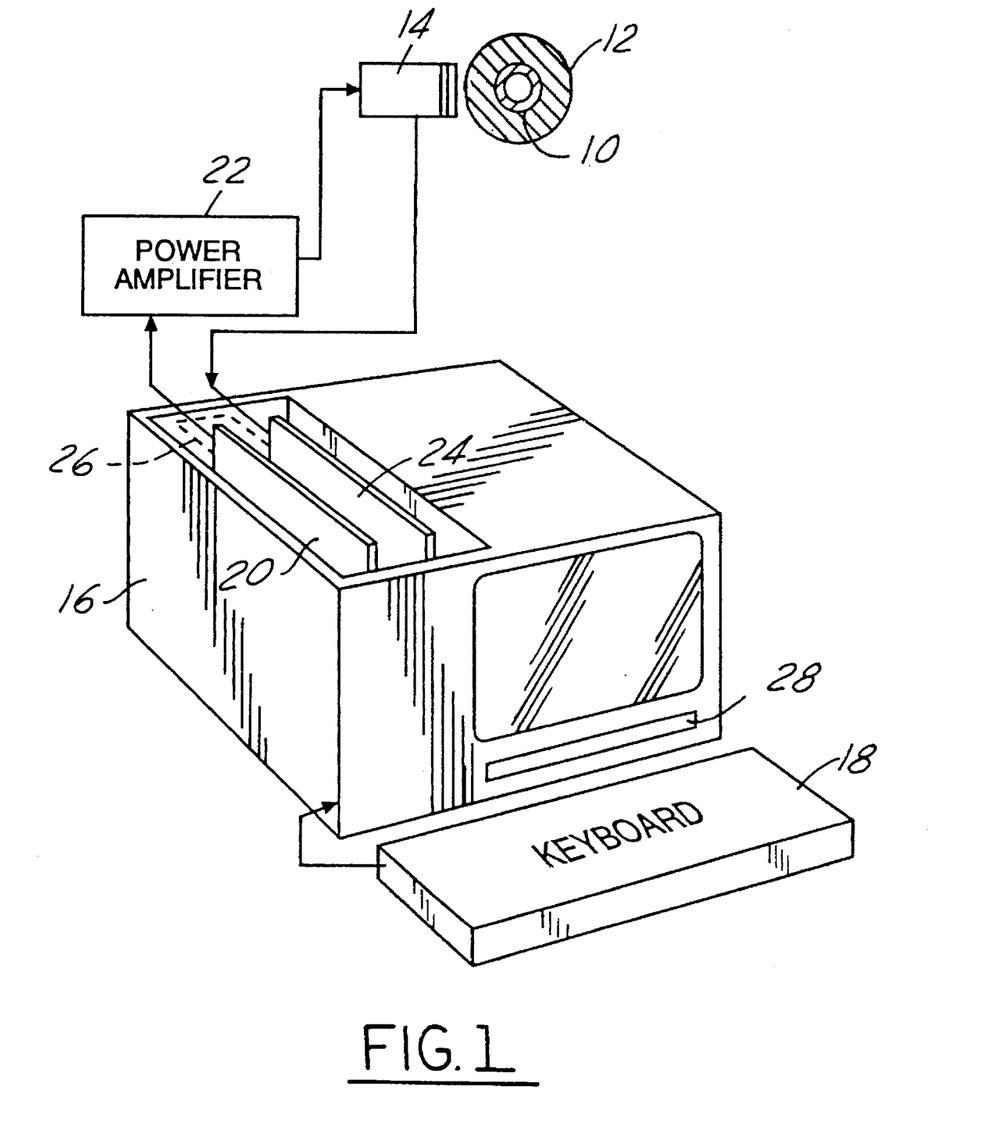
FIG. 1 is a diagram diagrammatically showing the interconnections of components of an apparatus of the invention.

FIG. 1 diagrammatically illustrates selected interconnected components for constructing an apparatus for performing methods associated with this invention, namely for non-invasively therapeutically treating bone tissue in vivo, to stimulate bone growth (ingrowth) and bone healing. These components are, in general, commercially available from different sources and will be identified as the detailed description of their total operation is provided.

Referring now to FIG. 1, the bone locale 10, such as a fracture site, an area affected by osteoporosis, or any other part of bone tissue to be treated non-invasively, is shown surrounded by soft tissue 12. Ultrasonic transducer 14 is placed near bone locale 10, adjacent soft tissue 12. By way of example, transducer 14 can be a rectangular piezoelectric transducer of approximately one by two inches placed on the surface of the skin overlying the fractured bone at approximately the site of fracture. The transducer may have a single piezoelectric element that is adapted for both transmitting and receiving, or one transmitting element and one or more receiving elements (not specifically shown). Such transducers are available from Parallel Designs, Inc., Phoenix, Ariz. As shown, transducer 14 is used for signal launching and receiving the launched signals after reflecting back from bone 10 and passing through surrounding soft tissue 12. An ultrasonic couplant (not shown) such as a gel is applied between transducer 14 and the patient's outer skin surrounding the soft tissue 12.

Basic operation is governed by a signal processing unit 16, which specifically may be a computer, and more specifically, a personal computer, such as the 66 MHz Pentium available from Gateway 2000, Inc., North Sioux City, S. Dak. As its designation suggests, this computer contains a 66 MHz clock-pulse generator, and an Intel 586 (Pentium) processor, with provision for keyboard instructions at 18. Computer 16 performs constant on-line monitoring of proper functioning of the apparatus according to the present invention. Specifically, computer 16 ensures providing a prescribed therapy to a patient by responding to and watching the reflected signals to calculate an appropriate treatment dose of ultrasonic exposure.

A sinusoidal function-generator at a card 20 is relied upon to generate an excitation signal, which is supplied to launch transducer 14, via power amplifier means 22. The power amplifier is suitably Model No. 2401, an RF power amplifier product of EIN, Inc., Rochester, N.Y. This product provides a 50 dB gain over the range 20 kHz to 10 MHz.

The excitation signal produced by the generator at card 20 is a pulsed sine wave signal in the ultrasonic range to about 2 MHz, which is sine wave modulated in the range of 0 to 25 kHz. The generator at card 20 may suitably be a commercially available waveform synthesizer, a product of Quatech, Inc., Akron, Ohio, identified by Quatech part No. WSB-100. This waveform synthesizer provides generation of analog signals independent of host computer 16, allowing full processor power to be used for other tasks, including calculation of waveform data. Card 20 preferably has the capacity to generate an output signal comprising literally thousands of points in the indicated ultrasonic frequency range.

Another card 24 is also shown installed in computer 16, for converting analog signals obtained from the receiving element of transducer 14 into digital format for further processing in computer 16. A known in the art switching element (not shown) can be used for disconnecting transducer 14 from card 20 and connecting it to card 24 which latter card may suitably contain a 100 MHz waveform digitizer, part number STR*8100, a product available from SONIX, of Springfield, Va. A connection 25 (shown by broken lines) connects signal-generator card 20 to A/D card 24, for synchronizing purposes and for the purposes of digitizing the reflected waveform, to enable computer 16 to perform a suitably compensated, continuously operative updating average of the signals received at transducer 14. A conventional preamplifier (not shown) for increasing the level of the reflected waveform before being input to card 24 can be included.

In order to obtain an estimate of the thickness of the traversed soft tissue overlying the fracture site and properly adjust the amplitude of the therapeutic ultrasonic signal, an initial interrogating acoustic ultrasonic pulse is preliminarily transmitted by card 20 via transducer 14. An exponentially damped sinusoidal signal at 1.1 MHz, with a duration of about 2 μs could be an example of such a pulse. Transducer 14 is then used as a receiver to record the reflected signal from the near bone surface. The arrival time of the reflected signal provides a measure of the round-trip transit time, τ, for the acoustic pulse to travel from the transducer through the soft tissue to the bone surface (where it is partially reflected), and back through the soft tissue. The soft-tissue thickness, $d_s$, can then be calculated as $d_s = v_s \tau / 2$ where $v_s$ is the velocity of ultrasound in soft tissue and is given by $v_s = 1540$ ms$^{-1}$.

Once an estimate of soft tissue thickness is obtained, it may be used for adjusting the input signal amplitude to ultrasonic transducer 14 to ensure that the optimal power intensity impinges on the fractured bone. This is preferably carried out as follows. Through a reflection measurement, an above mentioned estimate of soft tissue thickness, $d_s$ [cm], is acquired. Then, according to, for example, *Biomedical Ultrasonics*, by P.N.T. Wells, Academic Press, London, 1977, a nominal value for ultrasonic attenuation at 1.1 MHz in soft tissue can be obtained as $\alpha_s \approx 1$ dB/cm. Thus, for a soft tissue thickness given by $d_s$, the total decrease in signal amplitude, $\Delta \alpha$ in dB at the bone surface is $\Delta \alpha = \alpha_s d_s$.

The following formula may then be used to construct a look-up table which provides the necessary values for the relative amplification, A, applied to the input signal. The signal amplification is calculated from $A = 10^{(\Delta \alpha / 20)}$.

For example, the associated input signal amplifications to be used may be calculated for a range of soft tissue thicknesses:

| Soft Tissue Thickness [cm] | Signal Amplification |
|---|---|
| 1 | 1.12 |
| 2 | 1.26 |
| 3 | 1.41 |
| 4 | 1.58 |
| 5 | 1.78 |
| 6 | 2.00 |

It is noted that these signal amplifications are relative to the nominal signal value used for producing the desired power density (intensity $I_{SATA}=45$ mW/cm$^2$), within the near field of the ultrasound transducer in a medium of negligible attenuation, such as water. It should also be noted that for safety considerations, it may not be possible to use arbitrarily large incident power intensities (at the skin surface), which may, for example, be needed in case of excessively thick soft tissue overlying the fractured bone. In these cases, a maximum power intensity will be specified a priori; anything above this value will be saturated to this maximum intensity.

The therapeutic signal is specifically designed to optimally stimulate the fracture healing process. The optimal signal characteristics, which are set forth in more detail below, are derived using nonlinear wave-propagation theory and stimulate bone healing and growth through its direct effect on fluid flow. The reliance on acoustic microstreaming as the primary bio-effective aspect of the endogenous ultrasonic signal has led to a more effective and efficacious treatment for bone repair, in contrast to the prior art, which relies on, for example, the endogenous piezoelectricity of bone (see Duarte, supra), the generation of mechanical strains in the bone tissue (see Basserr etal., U.S. Pat. Nos. 4,928,959 and 5,046,484, and McLeod etal., supra), or on the induction of electrical currents in bone tissue (see Ryaby et al., U.S. Pat. No. 4,266,533).

For better understanding the fluid flow nature of the ultrasound stimulation of bone growth and repair, it should be taken into consideration that the induction of fluid flow arises out of a complex set of interactions of the externally applied ultrasonic signal with the bone tissue. The interactions can be characterized using a generalized theory of acoustics in porous media that includes the effects of an ionic fluid in the pore spaces, as exists in bone tissue. A summary of this theory given below provides the basis for which the optimal ultrasonic therapeutic signals are derived.

Fluid flow is assumed to be the fundamental entity which, when stimulated, will enhance bone growth and healing. In what follows, $\underline{w}$ is defined to be the displacement vector of the fluid relative to the solid matrix (known also as specific discharge relative to the solid) and $\xi=-\nabla\cdot\underline{w}$ is the increment of the fluid content per unit volume of the medium. Here $\nabla$ is the nabla operator, and $(\cdot)$ is the scalar product. Therefore, $\psi_E\cdot\underline{n}=(\partial\underline{w}/\partial t)\cdot\underline{n}$ is the Eulerian flux (ms$^{-1}$) of fluid crossing a unit area whose normal unit vector is $\underline{n}$. (This flux is related to the fluid flow in acoustic microstreaming) In this case, $\partial\xi/\partial t$ is the net fluid flux entering the unit volume fluid influx).

A generalized Darcy equation can be used to express the relationship between fluid flux and related quantities in the porous medium by taking into account the contribution of Maxwell's stress tensor in the fluid:

$$\left(\frac{\eta}{k_0}+\frac{\alpha_\infty \rho_F}{f_0}\frac{\partial}{\partial t}\right)\frac{\partial \underline{w}}{\partial t} \cong -\nabla p_F + \epsilon_F(\nabla^2\phi_F)\nabla\phi_F +$$

-continued $$\frac{\epsilon_F^2}{6\epsilon_0}\nabla(\nabla\phi_F\cdot\nabla\phi_F)$$

In this expression, $\eta$ (kgm$^{-1}$s$^{-1}$) is the viscosity of the fluid, $\alpha_\infty$ is the (high frequency) tortuosity of the porous medium, $k_o$ (m$^2$) is the (low frequency) Darcy permeability, $\epsilon_F$ and $\epsilon_o$ (Fm$^{-1}$) are the dielectric permittivities of the fluid and vacuum, respectively ($\epsilon_F \gg \epsilon_o$), $f_o$ is the volummetric porosity, and $\rho_F$ (kgm$^{-3}$) is the fluid density. The function $\phi_F$ (V) is the scalar electric potential in the fluid that results from the perturbation of the endogenous electric potential by the exogenous acoustic exposure (i.e., the ultrasonic signal). The endogenous electric potential arises from several sources, including primarily the interaction of the ionic fluid with the charged solid matrix surface. It also should be noted that the electric field within the fluid is equal to $-\nabla\phi_F$ (Vm$^{-1}$). The pressure in the fluid is denoted by $p_F$ (Nm$^{-2}$), and is the pressure resulting from the interaction of the exogenous acoustic exposure with the fluid-filled porous bone structure.

After some reasonable simplifying assumptions and using "$\langle\rangle$" to denote time average, the previous equation can be used to express the time average Eulerian fluid (streaming) flux as a function of the time average fluid pressure and electric potential as:

$$\langle\psi_E\rangle = \left\langle\frac{\partial w}{\partial t}\right\rangle \cong -\frac{k_0}{\eta}\nabla\langle p_F\rangle +$$

$$\frac{k_0}{\eta}\frac{\epsilon_F}{2}\left(1+\frac{\epsilon_F}{3\epsilon_0}\right)\nabla\langle\nabla\phi_F\cdot\nabla\phi_F\rangle$$

This equation demonstrates that the average Eulerian flux of fluid in the porous medium is dependent on the electric field squared, and that the latter's spatial variation can give rise to a non-zero mean (or net) fluid flux irrespective of the time waveform of the perturbation induced by the ultrasound exposure on the electric field $-\nabla\phi_F$. Moreover, the steady component of the fluid flux occurs whether or not the applied mean pressure (i.e., time average) is zero, as may arise for example, with the ultrasonic input.

Some of the equations necessary to evaluate all the components of the acoustic field are omitted, as the details are quite cumbersome and do not add additional insight into the results presented above. It should be noted that the net average fluid flux entering the unit volume is zero, i.e., $$\left\langle\frac{\partial\xi}{\partial t}\right\rangle = 0$$

thus providing an alternating pulsarils fluid influx.

It should also be pointed out that the theory presented can also characterize two other sources of nonlinearity in the interaction of the ultrasonic signal with the bone tissue. The first is related to convective flow and is one source of the well-known "radiation pressure" exerted by an acoustic wave. This phenomenon arises from hydrodynamical considerations, and in the notation used may be written as $$\underline{\psi}_L \equiv \frac{d\underline{w}}{dt} = \frac{\partial\underline{w}}{\partial t} + (\underline{\psi}_L\cdot\nabla)\underline{w} = \underline{\psi}_E + (\underline{\psi}_L\cdot\nabla)\underline{w}$$

where $\psi_L$ is the material of Lagrangian fluid (streaming) flux and $(\psi_L\cdot\nabla)\underline{w}$ is the convective nonlinearity.

Another source of nonlinearity and one which may also be incorporated into the fundamental theory arises due to the constitutive relationship between pressure and density, namely $$p_F \equiv p_{Fo} + A\left[\frac{\rho_F - \rho_{F0}}{\rho_{F0}} + \frac{B}{2A}\left(\frac{\rho_F - \rho_{F0}}{\rho_{F0}}\right)^2\right]$$

where $\rho_{Fo}$ and $p_{Fo}$ are the unperturbed fluid density and pressure, respectively, and A and B are the well-known nonlinear parameters of the fluid where B/A can typically be as large as 11. This relationship applies to the fluid phase. Analogously, a nonlinear constitutive relationship can also be written for the solid phase of the bone tissue, which will account for additional nonlinearities in the overall solution for fluid flux. Furthermore, the contribution of Maxwell's stress tensor to the solid matrix is another source of nonlinearity.

As may be seen readily from the describing equations, both constant and oscillatory fluid flows for promoting bone growth and repair can be stimulated through appropriate design of the applied acoustic signal that will be discussed below in more detail. The above theory clarifies that for obtaining both constant and oscillatory fluid flows at rates relevant to therapeutic bone dynamics, the leading term is the square of the applied ultrasonic signal p(t), i.e., $p^2(t)$. This nonlinearity enables the "in vivo" demodulation of the exogenous ultrasonic waveform, allowing it to have maximal therapeutical effects on bone growth and healing. The signals are specifically designed to be modulated by relatively high frequencies (generally above 500 Hz) in a pulsed excitation mode, which permits the bone tissue to respond maximally during each stimulatory cycle.

The foregoing aspects of the nonlinear acoustic theory provide the underlying basis for determining and thereby inducing fluid flow by the exogenous ultrasonic therapeutic signal.

It also should be noted that the received ultrasonic signal is used as a means for providing on-line fault detection, to ensure that the required therapeutic signal is reaching the fracture site during all periods of the treatment prescribed to a patient.

General signal-processing/display/storage software for the signal processing control and operation of computer 16 is not shown but will be understood to be contained on a conventional floppy disk loaded at 28 into computer 16; this software is suitably the MATLAB-386, available from The MathWorks, Inc., Natick, Mass. Further software (not illustrated) includes the signal processing toolbox, also available from MathWorks, as well as Fortran 5.0, available from Microsoft Corporation, Bothell, Wash., and LabView, available from National Instruments Corporation, Austin, Tex.

Figure 2:
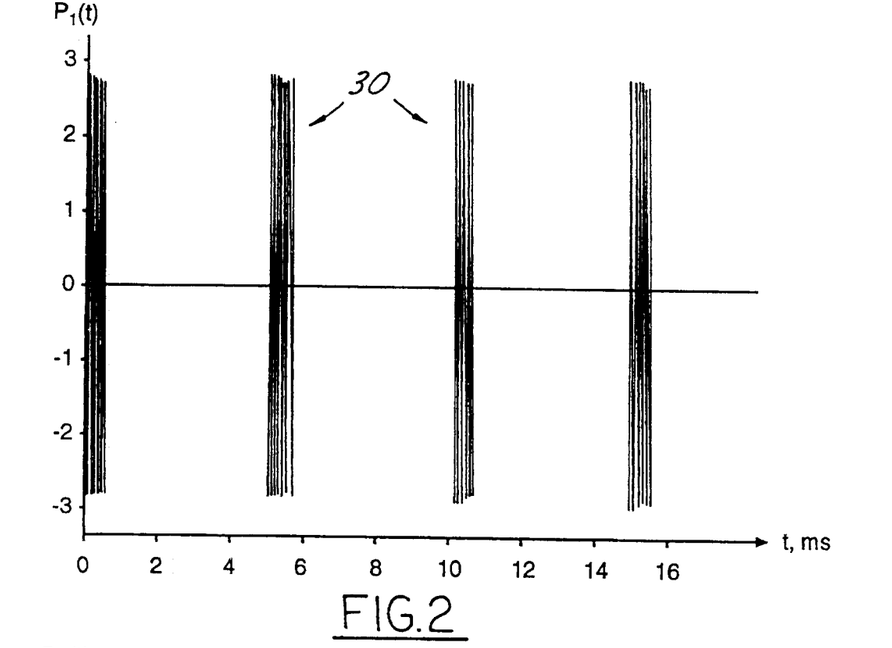
FIGS. 2, 3 and 4, respectively, illustrate a set of acoustic ultrasonic signals used for stimulation of bone growth and healing for several of the currently preferred embodiments.
Figure 3:
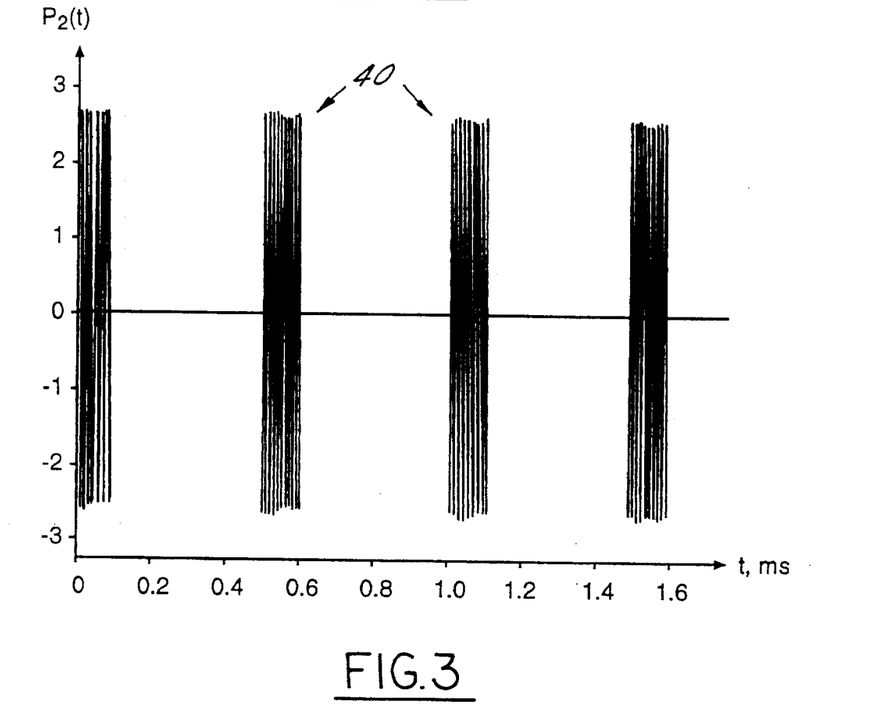
Figure 4:
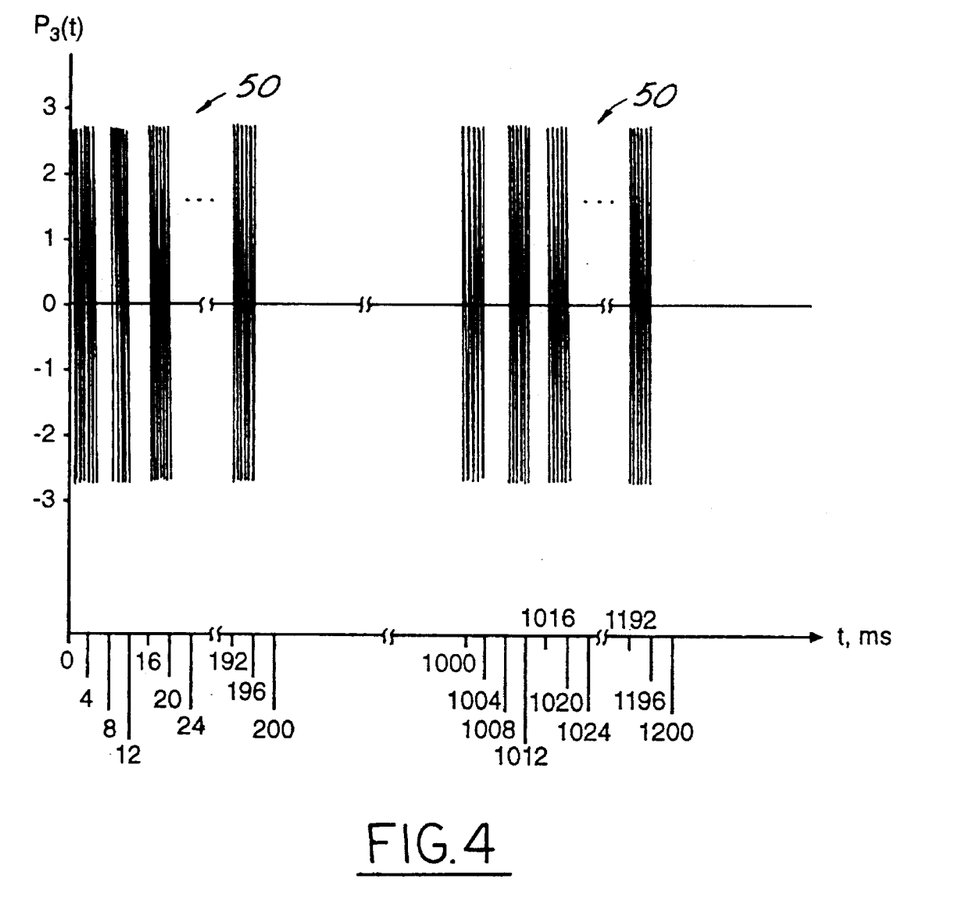

In the presently preferred embodiments of this invention and with additional reference to FIGS. 2, 3 and 4, showing the general outlook of the signals employed, without concrete details specifically regarding frequency and power parameters thereof, bony member 10 surrounded with soft tissue 12 is placed next to ultrasound transducer 14. An ultrasound signal is transmitted from transducer 14, passes through soft tissue 12, is partially transmitted into the bony member, and is partially reflected from bone tissue 10 back through soft tissue 12 to be received by the receiving element (not specifically shown) of transducer 14. The transmitted ultrasound signal is generated using a finite-duration sine-wave signal, which is sine-wave modulated. A single cycle of this waveform is described by $$p(t) = \sum_{i=0}^{N-1} p_s(t - iT_s'), \quad (1a)$$

repeating every T seconds (1/T Hz), where $p_s(t)$ is given by the following equation:

$$p_s(t) = \begin{cases} K\{1 + a\sin(2\pi f_m t)\}\sin(2\pi f_0 t), & 0 \leq t \leq T_s, \\ 0 & \text{otherwise,} \end{cases} \quad (1b)$$

In equations 1a and 1b, the range of signal parameter values are $0 \leq f_m \leq 25$ kHz (preferably without the zero value, i.e., in most cases $f_m \neq 0$), 25 kHz$<f_o \leq 2$ MHz, 0.2 ms$\leq T \leq 1.0$ s (corresponding to pulse repetition rates of 1 Hz–5 kHz), 0.1 ms$\leq T_2 <1.0$ s, 0.1 ms$<T_s \leq 1.0$ s (corresponding to a duty cycle, $\gamma = NT_s'/T$, or effective duty cycle taking into account the integrated "on-time" (the overall pulse durations) within a cycle, $\gamma = (T_{s1} + T_{s2} + \ldots + T_{sN})/T$, of $0.0001 \leq \gamma < 1$), $1 \leq N \leq 10,000$. The range of the modulation index, a, is given by $0 \leq a \leq 1000$. The constant K is adjusted so that the acoustic ultrasonic wave impinging at the near bone surface has an intensity ($I_{SATA}$) in the range of 20–100 mW/cm$^2$.

In a special case (N=1), where $p(t)=p_s(t)$, this waveform is described by $$p(t) = K\{1 + a\sin(2\pi f_m t)\}\sin(2\pi f_o t), \quad 0 < t < T_s,$$

repeating every T seconds, for a period of time preferably ranging from 5 minutes to 1 hour. The range of parameters is: $0 \leq f_m \leq 25$ kHz (preferably without the zero value, i.e., in most cases $f_m \neq 0$); 25 kHz$\leq f_o \leq 2$ MHz; 0.2 ms$\leq T \leq 1$ s (corresponding to pulse repetition rates of 1 Hz–5000 Hz) and 0.1 ms$\leq T_s \leq 1$ s (corresponding to a duty cycle, $\gamma = T_s/T$, of $0.0001 \leq y < 1$);. The constant K is adjusted such that an intensity ($I_{SATA}$) of the acoustic ultrasonic wave impinging at the near bone surface is in the range of 20–100 mW/cm$^2$.

Operating in the pulsed regime takes advantage of the acoustic nonlinearitttes when high amplitude waves are present. The maximum peak amplitude is K(1+a), and is constrained not to exceed normal safety levels. Amplitude modulation of the carrier signal at a relatively high frequency is specifically used to generate fluid flux at relatively high rates. For the preferred embodiments of this invention, the amplitude of the signal, as noted above, is adjusted to provide $I_{SATA}$ of approximately 45 mW/cm$^2$ at the fracture site.

It is noted that dynamic strains induced in the bone tissue are primarily in the ultrasonic spectral region, that is, at the nominal frequency of the applied ultrasonic signal. For the presently preferred embodiment, this frequency is 1.1 MHz, and in all cases is above 25 kHz. Additionally, the strain levels induced in the bone tissue, assuming a characteristic length of 10 centimeters, are extremely small. The peak-to-peak strain value can be reasonably well approximated from the well known equation for induced particle displacements associated with an ultrasonic input (see for example *Physical Principles of Medical Ultrasonics*, ed., CR Hill, Halsted Press, 1986, p. 57). The particle displacement, D, is given by $$D = 1/(\pi f) I^{1/2}/(\rho_o c/2)^{1/2}$$

where I is the ultrasonic power intensity in the bone tissue, $\rho_o$ is the unperturbed bone density, c is the velocity of ultrasound in the bone, and f is the ultrasonic frequency. Using values associated with bone, and for the preferred ultrasonic signal embodiments, a value of D of about 0.016 microns (at 1.1 MHz) can be obtained, and therefore the induced peak-to-peak strain is found to be less than about 0.2 microstrain.

For the purposes of the present invention, the three presently preferred embodiments include ultrasonic signals that are specified as follows:

1. As illustrated in FIG. 2, signal 30 is repeated at a repetition rate of 200 Hz (T=5 ms). A single cycle of the waveform is a 0.5 ms duration sine wave of carrier frequency 1.1 MHz modulated by a 20 kHz sine wave, followed by 4.5 ms of "off time", with the modulation index, a=0.3. This signal is described by the following equation:

$$p_1(t) = \begin{cases} K\{1 + 0.3\sin(2\pi \cdot 20 \cdot 10^3 t)\}\sin(2\pi \cdot 1.1 \cdot 10^6 t), \\ \qquad\qquad\qquad\qquad 0 \leq t \leq 0.5 \text{ ms} \\ 0 \qquad\qquad\qquad 0.5 \text{ ms} < t \leq 5 \text{ ms} \end{cases}$$

repeating at 200 Hz, and K is adjusted so that $I_{SATA}=45$ mW/cm$^2$.

2. As illustrated in FIG. 3, signal 40 is repeated at a repetition rate of 2000 Hz (T=0.5 ms). A single cycle of the waveform is a 0.1 ms duration sine wave of carrier frequency 1.1 MHz modulated by a 20 kHz sine wave, followed by 0.4 ms of "off time", with the modulation index, a=0.3. This signal is described by the following equation:

$$p_2(t) = \begin{cases} K\{1 + 0.3\sin(2\pi \cdot 20 \cdot 10^3 t)\}\sin(2\pi \cdot 1.1 \cdot 10^6 t), \\ \qquad\qquad\qquad\qquad 0 \leq t \leq 0.1 \text{ ms} \\ 0 \qquad\qquad\qquad 0.1 \text{ ms} < t \leq 0.5 \text{ ms} \end{cases}$$

repeating at 2000 Hz, and K is adjusted so that $I_{SATA}=45$ mW/cm$^2$.

3. As illustrated in FIG. 4, signal 50 is repeated at a repetition rate of 1 Hz. A single cycle of the waveform consists of 25 repetitions (N=25) of a 4 ms duration ($T_s$=4 ms) 1.1 MHz sine wave modulated by a 5 kHz sine wave ($f_m$=5 kHz), each such 4 ms "on time" being followed by 4 ms of signal "off time" ($T_s$=8 ms). The entire sequence of 25 sinusoidally modulated sinusoidal pulses, together with their associated 4 ms "off times", lasts for 200 ms, after which time the signal is off for 800 ms. The sequence is then repeated at 1 second intervals (1 Hz), the modulation index being a=0.3. This signal is described by the following equation:

$$p_3(t) = \sum_{i=0}^{24} p_s(t - i \cdot 8 \text{ ms}), \text{ repeating at 1 Hz,}$$

where $$p_s(t) = \begin{cases} K\{1 + 0.3\sin(2\pi \cdot 5 \cdot 10^3 t)\}\sin(2\pi \cdot 1.1 \cdot 10^6 t), & 0 \leq t \leq 4 \text{ ms} \\ 0 & \text{elsewhere} \end{cases},$$

and K is adjusted so that $I_{SATA}=45$ mW/cm$^2$.

In order to synthesize the second signal of the presently preferred embodiments, the above-mentioned Quatech card is used in conjunction with another instrument, suitably a Wavetek Model No. 178 Programmable Waveform Synthesizer available from Wavetek, San Diego, Calif. In this case, the Quatech card outputs the modulating waveform as input to the Wavetek Waveform Synthesizer to amplitude modulate the 1.1 MHz carrier signal.

An enlarged class of ultrasonic therapeutic signals includes waveforms, which are frequency modulated in addition to them being amplitude modulated in order to take further advantage of the nonlinear propagation characteristics of bone tissue. In this case, sweeping not only the modulating frequency but also the carrier frequency contributes both to changing and manipulating so-called hot and cold spots in ultrasonic treating a tissue, and to bringing energy to a bone at different frequencies. These things considered, the efficiency of treating bone tissues in accordance with the present invention is additionally increased.

The waveforms of this class can be described as follows:

$$p(t) = \sum_{i=0}^{N-1} p_s(t - iT_s'), \qquad (2a)$$

repeating every T seconds, where $P_s(t)=K\{1+a \sin[2\pi(f_m+(f_m^*-f_m)t/T_s)t]\sin[2\pi(f_o+(f_o^*-f_o)t/T_s)t]\}$, (2b) $0 \leq t \leq T_s$, where all the parameters are contained in the same ranges as defined before, $f_m^*$ and $f_o^*$ define the upper limit values of sweeping for modulating and carrier frequencies, respectively, with $f_m \leq f_m^* < 25$ kHz and $f_o \leq f_o^* = 2$ MHz.

For the purposes of the present invention, the presently preferred embodiment of this class of signals include an ultrasonic waveform that is specified as follows, with $f_o^*=f_o=1.1$ MHZ, $f_m=500$ Hz, and $f_m^*=2000$ Hz:

$$p_4(t) = \sum_{i=0}^{24} p_s(t - i \cdot 8 \text{ ms}),$$

where $$p_s(t) = \begin{cases} K\{1 + \sin[2\pi(500 + (2000-500)t/4\text{ms})t]\sin[2\pi \cdot 1.1 \cdot 10^6 t]\}, \\ \qquad\qquad\qquad\qquad 0 \leq t \leq 4 \text{ ms} \\ 0 \qquad\qquad\qquad \text{elsewhere} \end{cases},$$

and K is adjusted so that $I_{SATA}=45$ mW/cm$^2$.

From the aforesaid it follows that according to the present invention the following four types of signals could be employed in its implementation, with the specific parameters discussed in the above:

— sine wave modulated sine wave signals;
— swept sine wave modulated sine wave signals;
— sine wave modulated swept sine wave signals;
— swept sine wave modulated swept sine wave signals.

For the purposes of this invention, a sine wave can be assumed to be used to denote a sinusoidal function at a single frequency or a sinusoidal function with frequency modulation, i.e., a swept sine wave. It is also appreciated that for most cases the modulating frequency in these signals is not supposed to assume the zero value. However, in some concrete instances it can begin or end at or pass through this value.

The main and important advantages of the present invention can be summarized as follows:

— the reliance on fluid flow as the primary bio-physical phenomenon related to bone growth, which is affected in a near optimal fashion by the ultrasonic signal;

— the use of an analytic model for characterizing ultrasonic wave propagation in a porous medium such as bone, in order to establish the biophysical parameters of interest (i.e., fluid flow), in comparison to the prior art, which used either experimental observations only or ad hoc approaches;

— the use of relatively high frequency (preferably greater than 500 Hz and less than 25 kHz) sinusoidal amplitude modulation as a means for directly affecting fluid flow;

— the use of a relatively low carrier frequency, allowing greater soft tissue and bone penetration due to significantly decreased signal attenuation;

— the use of a repetitive stimulation, emulating physiological loading;

— the ability to construct the device with components that are largely commercially available;

— the use of reflection measurements to estimate actual soft tissue thickness, to thereby adjust the amplitude level (i.e., dose) appropriate for each patient and to provide on-line fault detection.

It should be understood that though the apparatus and method in accordance with the present invention have been described in detail they may be subjected to modifications and other embodiments incorporating the inventive features. Specifically, the apparatus can be constructed with the use of analog components alone, in order to reduce significantly the overall cost and complexity. Accordingly, it is intended that the foregoing disclosure is to be considered as illustrating the principles of the invention as an example of those features and not as a delimiting descriptions which is the purpose of the claims that follow.

What is claimed is:

1. A method of non-invasively therapeutically treating a bone tissue in vivo using an ultrasonic signal, comprising the steps of:

(A) producing a periodic therapeutic sine-wave modulated ultrasonic sine-wave signal described by $$p(t) = \sum_{i=0}^{N-1} p_s(t - iT_s'),$$

$$p_s(t) = \begin{cases} K\{1 + a\sin(2\pi f_m t)\}\sin 2\pi f_0 t, & 0 \leq t \leq T_s, \\ 0 & \text{otherwise,} \end{cases}$$

where N is the number of pulse repetitions within each cycle and $1 < N < 10,000$, $f_m$ is the modulating frequency which is selected within the range of $0 < f_m < 25$ kHz; $f_o$ is the carrier frequency which is selected within the range of 25 kHz$< f_o <$2 MHz; T is the cycle duration which is 0.2 ms$<$T$<$1.0 s; $T_s$ is the pulse width which is 0.1 ms$<T_s<$1.0 s; $T_s'$ is the duration of a pulse and a pause for one repetition (N=1) which is 0.1 ms$<T_s'<$1.0 s; a is the modulation index which is $0<a<1000$; K is a constant defining intensity ($I_{SATA}$) of said ultrasonic signal; and (B) exposing said bone tissue to said therapeutic ultrasonic signal transmitted through soft tissue overlying said bone tissue;

to thereby induce bone growth and bone healing.

2. The method of non-invasively therapeutically treating a bone tissue in vivo according to claim 1, further comprising the step of:

(C) preselecting said intensity of said therapeutic signal.

3. The method of non-invasively therapeutically treating a bone tissue in vivo according to claim 2, wherein said step (C) comprises the substeps of:

generating an interrogating ultrasonic pulse;

transmitting said interrogating ultrasonic pulse to said bone tissue through said soft tissue overlying said bone tissue;

receiving a portion of said interrogating pulse reflected from said bone tissue;

determining the thickness of said soft tissue using said reflected portion; and adjusting the amplitude of said therapeutic ultrasonic signal to ensure that spatial-average time-average intensity thereof reaching said bone tissue is in a predetermined range of 20–100 mW/cm$^2$.

4. The method of non-invasively therapeutically treating a bone tissue in vivo according to claim 3, wherein said thickness of said soft tissue is calculated as $d_s = v_s \tau/2$ where $d_s$ is the desired thickness; $v_s$ is the velocity of ultrasound in soft tissue; and $\tau$ is a round-trip transit time for said acoustic pulse to travel from a source thereof through the soft tissue, to the bone tissue, and back through the soft tissue.

5. The method of non-invasively therapeutically treating a bone tissue in vivo according to claim 3, wherein said initial interrogating ultrasonic pulse is an exponentially damped sinusoidal signal at 1.1 MHz, with a duration of about 2 µs.

6. The method of non-invasively therapeutically treating a bone tissue in vivo according to claim 1, wherein said $p_s(t)$ has the form of $$p_s(t) = \begin{cases} K\{1 + 0.3\sin(2\pi \cdot 20 \cdot 10^3 t)\}\sin 2\pi \cdot 1.1 \cdot 10^6 t, \\ \qquad 0 \leq t \leq 0.5 \text{ ms,} \\ 0 \qquad 0.5 \text{ ms} < t \leq 5 \text{ ms,} \end{cases}$$

with the number N of pulse repetitions within each cycle being 1, the carrier frequency $f_o$ being 1.1 MHz, the modulating frequency $f_m$ being 20 kHz, the modulation index a being 0.3, the pulse width $T_s$ being 0.5 ms, the cycle duration T being 5 ms, and the intensity $I_{SATA}$ being 45 mW/cm$^2$.

7. The method of non-invasively therapeutically treating a bone tissue in vivo according to claim 1, wherein said $p_s(t)$ has the form of $$p_s(t) = \begin{cases} K\{1 + 0.3\sin(2\pi \cdot 20 \cdot 10^3 t)\}\sin 2\pi \cdot 1.1 \cdot 10^6 t, \\ \qquad 0 \leq t \leq 0.1 \text{ ms,} \\ 0 \qquad 0.1 \text{ ms} < t \leq 0.5 \text{ ms,} \end{cases}$$

with the number N of pulse repetitions within each cycle being 1, the carrier frequency $f_o$ being 1.1 MHz, the modulating frequency $f_m$ being 20 kHz, the modulation index a being 0.3, the pulse width $T_s$ being 0.1 ms, the cycle duration T being 0.5 ms, and the intensity $I_{SATA}$ being 45 mW/cm$^2$.

8. The method of non-invasively therapeutically treating a bone tissue in vivo according to claim 1, wherein said periodic therapeutic sine-wave modulated ultrasonic sine-wave signal has the form of $p(t) = p_s(t) = K\{1 + a\sin(2\pi f_m t)\}\sin(2\pi f_o t)$, $0 < t < T_s$, with the number N of pulse repetitions within each cycle being 1, and an intensity $I_{SATA}$ being in the range of 20–100 mW/cm$^2$.

9. The method of non-invasively therapeutically treating a bone tissue in vivo according to claim 1, wherein said periodic therapeutic sine-wave modulated ultrasonic sine-wave signal is described by $$p(t) = \sum_{i=0}^{24} p_s(t - i \cdot 8 \text{ ms}), \text{ repeating at 1 Hz,}$$

with $p_s(t)$ given by the equation:

$$p_s(t) = \begin{cases} K\{1 + 0.3\sin(2\pi \cdot 5 \cdot 10^3 t)\}\sin 2\pi \cdot 1.1 \cdot 10^6 t, \\ \qquad 0 \leq t \leq 4 \text{ ms,} \\ 0 \qquad \text{elsewhere} \end{cases}$$

having the carrier frequency $f_o$ of 1.1 MHz, the modulating frequency $f_m$ of 5 kHz, the modulation index a of 0.3, the pulse width $T_s$ of 4 ms, the duration $T_s'$ of a pulse and a pause for one repetition being 8 ms, the number N of pulse repetitions within a cycle being 25, the cycle duration T of 1 s, and the intensity $I_{SATA}$ of 45 mW/cm$^2$.

10. The method of non-invasively therapeutically treating a bone tissue in vivo according to claim 1, wherein said intensity of said ultrasonic signal is selected in the range of 20 mW/cm$^2 \leq I_{SATA} <$ 100 mW/cm$_2$.

11. The method of non-invasively therapeutically treating a bone tissue in vivo according to claim 1, further comprising the step of (D) maintaining said exposing between about 5 minutes and about 1 hour.

12. The method of non-invasively therapeutically treating a bone tissue in vivo according to claim 11, further comprising the step of (E) repeating said exposing for about 1 to 3 times a day.

13. A method of non-invasively therapeutically treating a bone tissue in vivo using an ultrasonic signal, comprising the steps of:

(A) generating a periodic therapeutic frequency modulated sine wave amplitude modulated frequency modulated sine wave ultrasonic signal;

(B) selecting a power intensity of said therapeutic signal by virtue of (Ba) generating an interrogating ultrasonic pulse, (Bb) transmitting said interrogating ultrasonic pulse to said bone tissue through said soft tissue overlying said bone tissue, (Bc) receiving a portion of said interrogating pulse reflected from said bone tissue, (Bd) determining the thickness of said soft tissue using said reflected portion, and (Be) adjusting the amplitude of said therapeutic ultrasonic signal to ensure that a spatial-average time-average power intensity thereof reaching said bone tissue corresponds to a predetermined value; and ( C) exposing said bone tissue to said therapeutic ultrasonic signal transmitted through soft tissue overlying said bone tissue;

to thereby induce bone growth and healing.

14. The method of non-invasively therapeutically treating a bone tissue in vivo according to claim 13, wherein a duration of exposure being between about 5 minutes and about 1 hour for 1 to 3 times a day and said periodic therapeutic ultrasonic signal is amplitude modulated and has a carrier frequency of between about 25 kHz and about 2 MHz, a modulating frequency of up to about 25 kHz, a modulation index being selected in a range between 0 and 1000, and an intensity being in the range of 20–100 mW/cm$^2$.

15. The method of non-invasively therapeutically treating a bone tissue in vivo according to claim 14, wherein said amplitude modulated signal has the carrier frequency of 1.1 MHz, the modulating frequency of 20 kHz, the modulation index of 0.3, the pulse width of 0.5 ms, the cycle duration of 5 ms, and the intensity of 45 mW/cm$^2$.

16. The method of non-invasively therapeutically treating a bone tissue in vivo according to claim 14, wherein said amplitude modulated signal has the carrier frequency of 1.1 MHz, the modulating frequency of 20 kHz, the modulation index of 0.3, the pulse width of 0.1 ms, the cycle duration of 0.5 ms, and the intensity of 45 mW/cm$^2$.

17. The method of non-invasively therapeutically treating a bone tissue in vivo according to claim 14, wherein said amplitude modulated signal has:

a pulse width of between about 0.1 ms and about 1.0 s, a duration of a pulse and a pause for one repetition of between about 0.1 ms and about 1.0 s, a number of pulse repetitions within a cycle of up to 5000, and a cycle duration of between about 0.2 ms and about 1.0 s.

18. The method of non-invasively therapeutically treating a bone tissue in vivo according to claim 14, wherein said amplitude modulated signal has the carrier frequency of 1.1 MHz, the modulating frequency of 5 kHz, the modulation index of 0.3, the pulse width of 4 ms, the duration of a pulse and a pause for one repetition of 8 ms, the number of pulse repetitions within a cycle of 25, the cycle duration of 1 s, and the intensity of 45 mW/cm$^2$.

19. The method of non-invasively therapeutically treating a bone tissue in vivo according to claim 13, wherein a duration of exposure being between about 5 minutes and about 1 hour for 1 to 3 times a day and said periodic therapeutic ultrasonic signal has a carrier frequency with a selected value in the range between about 25 kHz and about 2 MHz and with a sweeping range between the selected value and about 2 MHz;

a modulating frequency with a selected value in the range up to about 25 kHz, and with a sweeping range between the selected value and about 25 kHz;

a modulation index selected in a range between 0 and 1000, a pulse width between about 0.1 ms and about 1.0 s, a duration of a pulse and a pause for one repetition between about 0.1 ms and about 1.0 s, a number of pulse repetitions within a cycle up to 10,000, a cycle duration between about 0.2 ms and about 1.0 s, and an intensity in the range of 20–100 mW/cm$^2$.

20. The method of non-invasively therapeutically treating a bone tissue in vivo according to claim 19, wherein said periodic therapeutic ultrasonic signal has the carrier frequency of 1.1 MHz, the modulating frequency of 500 Hz, said modulating frequency sweeping range of between 500 Hz and 2000 Hz;

the modulation index of 1, the pulse width of between 4 ms, the duration of a pulse and a pause for one repetition of 8 ms, the number of pulse repetitions within a cycle of 25, the cycle duration of 1 s, and the intensity of 45 mW/cm$^2$.

21. The method of non-invasively therapeutically treating a bone tissue in vivo according to claim 13, wherein said thickness of said soft tissue is calculated as $$d_s = v_s \tau/2$$

where $d_s$ is the desired thickness; $v_s$ is the velocity of ultrasound in soft tissue; and $\tau$ is a round-trip transit time for said acoustic pulse to travel from a source thereof through the soft tissue, to the bone tissue, and back through the soft tissue.

22. The method of non-invasively therapeutically treating a bone tissue in vivo according to claim 13, wherein said initial interrogating ultrasonic pulse is an exponentially damped sinusoidal signal at 1.1 MHz, with a duration of about 2 μs.

23. An apparatus for non-invasively therapeutically treating bone tissue in vivo, comprising:

a waveform synthesizer for producing an initial interrogating acoustic ultrasonic signal to determine the thickness of a soft tissue overlying said bone tissue, and an excitation signal to be applied to said bone tissue, said excitation signal being a finite duration frequency modulated sine wave carrier signal with a frequency selected in the ultrasonic region within the range of between about 25 kHz and about 2 MHz and having a sweeping range between a selected value and an upper limit value of about 2 MHz, amplitude modulated by a frequency modulated sine wave signal with a modulating frequency selected between about 0 Hz and about 25 kHz and having a sweeping range between a selected value and an upper limit value of about 25 kHz, said excitation signal being repeated substantially in the range 1 to 5000 Hz;

an ultrasonic transducer having a transmitting element being connected to said waveform synthesizer and adapted for acoustic coupling to nearby skin and for conveying said interrogating and said excitation signals along an ascertained path to said bone tissue, a receiving element for receiving a reflected portion of said interrogating signal reflected from said bone tissue; and a computer coupled to said transducer and said receiving element, for adjusting said excitation signal responsive to said received reflected signal.

24. A method of non-invasively therapeutically treating a bone tissue in vivo using an ultrasonic signal, comprising the steps of:

(A) producing a periodic therapeutic ultrasonic signal described by $$p(t) = \sum_{i=0}^{N-1} p_s(t - iT_s'),$$

repeating every T seconds (1/T Hz), with $p_s(t)$ given by the equation:

$$p_s(t) = K\{1 + a \sin[2\pi(f_m + (f_m^* - f_m)t/T_s)t]\sin[2\pi(f_o + f_o^* - f_o)t/T_s)t\},$$

$$0 \leq t \leq T_s,$$

where $f_m$ is a modulating frequency selected within the range of $0 < f_m \leq 25$ kHz and having a sweeping range between a selected value $f_m$ and an upper limit value $f_m^*$ of about 25 kHz;

$f_o$ is a carrier frequency selected within the range of 25 kHz$< f_o \leq 2$ MHz and having a sweeping range between a selected value $f_o$ and an upper limit value $f_o^*$ of about 2 MHz;

T is the cycle duration which is 0.2 ms$\leq T \leq 1.0$ s;

$T_s$ is the pulse width which is 0.1 ms$\leq T_s \leq 1.0$ s;

$T_s'$ is the duration of a pulse and a pause for one repetition (N=1) which is 0.1 ms$< T_s' \leq 1.0$ s;

a number N of pulse repetitions within a cycle being up to 10,000;

a is the modulation index which is $0 \leq a \leq 1000$;

K is a constant defining intensity ($I_{SATA}$) of said ultrasonic signal which is adjusted so that 20 mW/cm$^2 \leq I_{SATA} \leq 100$ mW/cm$^2$; and (B) exposing said bone tissue to said therapeutic ultrasonic signal transmitted through a soft tissue overlying said bone tissue;

to thereby induce bone growth and healing.

25. The method of non-invasively therapeutically treating a bone tissue in vivo according to claim 24, wherein said periodic therapeutic ultrasonic signal is described by the equation $$p(t) = \sum_{i=0}^{24} p_s(t - i \cdot 8 \text{ ms}), \text{ repeating at 1 Hz,}$$

where $$p_s(t) = \begin{cases} K\{1 + \sin[2\pi(500 + (2000 - 500)t/4\text{ms})t]\sin[2\pi \cdot 1.1 \cdot 10^6 t]\}, \\ \qquad\qquad\qquad\qquad\qquad 0 \leq t \leq 4 \text{ ms,} \\ 0 \qquad\qquad\qquad\qquad\qquad \text{elsewhere} \end{cases}$$

with the carrier frequency $f_o$ being 1.1 MHz;

the modulating frequency fm being 500 Hz;

the frequency $f_m^*$ being 2000 Hz;

the modulation index a being 1;

the pulse width $T_s$ being 4 ms;

the duration $T_s'$ of a pulse and a pause for one repetition being 8 ms;

the number N of pulse repetitions within a cycle being 25;

the cycle duration T being 1 s; and the constant K being adjusted so that the intensity $I_{SATA}$ is 45 mW/cm$^2$.

26. The method of non-invasively therapeutically treating a bone tissue in vivo according to claim 24, further comprising the step of (C) maintaining said exposing between about 5 minutes and about 1 hour.

27. The method of non-invasively therapeutically treating a bone tissue in vivo according to claim 26, further comprising the step of (D) repeating said exposing for about 1 to 3 times a day.

28. The method of non-invasively therapeutically treating a bone tissue in vivo according to claim 24, further comprising the step of (E) preselecting an intensity of said periodic therapeutical ultrasonic signal.

29. The method of non-invasively therapeutically treating a bone tissue in vivo according to claim 28, wherein said step (E) comprises the substeps of:

(Ea) generating an interrogating ultrasonic pulse;

(Eb) transmitting said interrogating ultrasonic pulse to said bone tissue through said soft tissue overlying said bone tissue;

(Ec) receiving a portion of said interrogating ultrasonic pulse reflected from said bone tissue;

(Ed) determining a thickness of said soft tissue using said reflected portion; and (Ee) adjusting an amplitude of said therapeutic ultrasonic signal to ensure that said intensity thereof reaching said bone tissue is in a predetermined range of 20–100 mW/cm$^2$.

30. The method of non-invasively therapeutically treating a bone tissue in vivo according to claim 29, wherein said thickness of said soft tissue is calculated as $d_s = v_s \tau / 2$ where $d_s$ is the desired thickness; $v_s$ is the velocity of ultrasound in soft tissue; and $\tau$ is a round-trip transit time for said acoustic pulse to travel from a source thereof through the soft tissue, to the bone tissue, and back through the soft tissue.

31. The method of non-invasively therapeutically treating a bone tissue in vivo according to claim 29, wherein said interrogating ultrasonic pulse is an exponentially damped sinusoidal signal at 1.1 MHz, with a duration of about 2 μs.

32. A method of non-invasively therapeutically treating a bone tissue in vivo using an ultrasonic signal, comprising the steps of:

(A) generating a therapeutic ultrasonic signal;

(B) selecting an intensity of said therapeutic signal by virtue of (Ba) generating an interrogating ultrasonic pulse, (Bb) transmitting said interrogating ultrasonic pulse to said bone tissue through said soft tissue overlying said bone tissue, (Bc) receiving a portion of said interrogating pulse reflected from said bone tissue, (Bd) determining the thickness of said soft tissue using said reflected portion, and (Be) adjusting the amplitude of said therapeutic ultrasonic signal to ensure that a spatial-average time-average intensity thereof reaching said bone tissue corresponds to a predetermined value; and (C) exposing said bone tissue to said therapeutic ultrasonic signal transmitted through soft tissue overlying said bone tissue;

to thereby induce bone growth and healing.

33. The method of non-invasively therapeutically treating a bone tissue in vivo according to claim 32, wherein said interrogating ultrasonic pulse is an exponentially damped sinusoidal signal at 1.1 MHz, with a duration of about 2 μs.

34. The method of non-invasively therapeutically treating a bone tissue in vivo according to claim 32, wherein said thickness of said soft tissue is calculated as $d_s = v_s \tau / 2$ where $d_s$ is the desired thickness; $v_s$ is the velocity of ultrasound in soft tissue; and $\tau$ is a round-trip transit time for said acoustic pulse to travel from a source thereof through the soft tissue, to the bone tissue, and back through the soft tissue.

35. The method of non-invasively therapeutically treating a bone tissue in vivo according to claim 32, further comprising the step of (D) maintaining said exposing between about 5 minutes and about 1 hour.

36. The method of non-invasively therapeutically treating a bone tissue in vivo according to claim 35, further comprising the step of (E) repeating said exposing for about 1 to 3 times a day.

37. The method of non-invasively therapeutically treating a bone tissue in vivo according to claim 32, wherein said therapeutic ultrasonic signal is a periodic frequency-modulated-sine-wave-amplitude-modulated-by-a -frequency-modulated-sine-wave signal having a carrier frequency $f_o$ with a selected value in a range between about 25 kHz and about 2 MHz, and swept up to the value $f_o^*$ of about 2 MHz;

a modulating frequency $f_m$ with a selected value in a range up to about 25 kHz, and swept up to the value $f_m^*$ of about 25 kHz;

a modulation index a in a range between 0 and 1000, a pulse width $T_s$ of between about 0.1 ms and about 1.0 s, a duration $T_s'$ of a pulse and a pause for one repetition of between about 0.1 ms and about 1.0 s, a number N of pulse repetitions within a cycle of up to 10,000, a cycle duration T of between about 0.2 ms and about 1.0 s, and an intensity $I_{SATA}$ in a range of 20 mW/cm$^2$–100 mW/cm$^2$.

38. The method of non-invasively therapeutically treating a bone tissue in vivo according to claim 37, wherein the carrier frequency $f_o$ is 1.1 MHz;

the modulating frequency $f_m$ is 500 Hz, swept up to the $f_m^*$ value of 2000 Hz;

the modulation index a is 1;

the pulse width $T_s$ is 4 ms;

the duration $T_s'$ of a pulse and a pause for one repetition is 8 ms;

the number N of pulse repetitions within a cycle is 25;

the cycle duration T is 1 s; and the intensity $I_{SATA}$ is 45 mW/cm$^2$.

39. The method of non-invasively therapeutically treating a bone tissue in vivo according to claim 32, wherein said therapeutic ultrasonic signal is an amplitude modulated periodic signal having a carrier frequency $f_o$ of between about 25 kHz and about 2 MHz, a modulating frequency $f_m$ of up to about 25 kHz, a modulation index a in a range between 0 and 1000, a pulse width $T_s$ of between about 0.1 ms and about 1.0 s, a cycle duration T of between about 0.2 ms and about 1.0 s, and an intensity $I_{SATA}$ in a range of 20–100 mW/cm$^2$.

40. The method of non-invasively therapeutically treating a bone tissue in vivo according to claim 39, wherein the carrier frequency $f_o$ is 1.1 MHz, the modulating frequency $f_m$ is 20 kHz, the modulation index a is 0.3, the pulse width $T_s$ is 0.5 ms, the cycle duration T is 5 ms, and the intensity $I_{SATA}$ is 45 mW/cm².

41. The method of non-invasively therapeutically treating a bone tissue in vivo according to claim 39, wherein the carrier frequency $f_o$ is 1.1 MHz, the modulating frequency $f_m$ is 20 kHz, the modulation index a is 0.3, the pulse width $T_s$ is 0.1 ms, the cycle duration T is 0.5 ms, and the intensity $I_{SATA}$ is 45 mW/cm².

42. The method of non-invasively therapeutically treating a bone tissue in vivo according to claim 39, wherein a duration $T_s'$ of a pulse and a pause for one repetition is between about 0.1 ms and about 1.0 s, and a number N of pulse repetitions within a cycle is up to 10,000.

43. The method of non-invasively therapeutically treating a bone tissue in vivo according to claim 39, wherein the carrier frequency $f_o$ is 1.1 MHz, the modulating frequency $f_m$ is 5 kHz, the modulation index a is 0.3, the pulse width $T_s$ is 4 ms, the duration $T_s'$ of a pulse and a pause for one repetition is 8 ms, the number N of pulse repetitions within a cycle is 25, the cycle duration T is 1 s, and the intensity $I_{SATA}$ is 45 mW/cm².

* * * * *